US00PP29911P3

(12) United States Plant Patent
Hansen

(10) Patent No.: US PP29,911 P3
(45) Date of Patent: Nov. 27, 2018

(54) ***PHLOX* PLANT NAMED 'FASHIONABLY EARLY FLAMINGO'**

(50) Latin Name: ***Phlox* hybrid**
Varietal Denomination: Fashionably Early Flamingo

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 68 days.

(21) Appl. No.: 15/530,085

(22) Filed: Dec. 1, 2016

(65) Prior Publication Data

US 2018/0160602 P1 Jun. 7, 2018

(51) Int. Cl.
*A01H 5/02* (2018.01)

(52) U.S. Cl.
USPC ..... Plt./320
CPC ..... *A01H 5/02* (2013.01)

(58) Field of Classification Search
USPC ..... Plt./320
CPC ..... A01H 5/02; A01H 5/00; A01H 6/70
See application file for complete search history.

(56) References Cited

U.S. PATENT DOCUMENTS

PP28,487 P2 * 10/2017 Hansen ..... A01H 5/02 Plt./320
PP28,680 P2 * 11/2017 Hansen ..... Plt./320

OTHER PUBLICATIONS

Michell's 2015-16 Availability List Walters Gardens, Inc. retrieved on Nov. 29, 2017, retrieved from the Internet at http://www.michells.com/availabilities/Waltersavailability.pdf, pp. 1, 23 and 28 (Year: 2016).*

* cited by examiner

*Primary Examiner* — June Hwu

(57) ABSTRACT

A new and unique cultivar of garden *phlox* named *Phlox* 'Fashionably Early Flamingo' multi-stemmed, dense, slowly-spreading habit with bright-green, glossy, lanceolate leaves. Flowers are sweetly-fragrant, initially light lavender-pink flower faces becoming pale lavender with light purple eye zones beginning late spring, continuing for about five weeks and repeating through mid-fall. Foliage stays clean and resists mildew.

1 Drawing Sheet

Botanical classification: *Phlox* hybrid;
Variety denomination: 'Fashionably Early Flamingo'.

BACKGROUND OF THE INVENTION

The present invention relates to a new and distinct cultivar of *Phlox* plant, known as *Phlox* 'Fashionably Early Flamingo' and will be referred to hereafter by its cultivar name, 'Fashionably Early Flamingo', or the "new plant". The new plant was the result of a single seedling selection from the cross of *Phlox maculata* 'Alpha' (not patented) times *Phlox* 'Amethyst Pearl' U.S. Plant Pat. No. 28,487 performed at a wholesale perennial nursery in Zeeland, Mich. on Jun. 13, 2012. The new plant was originally given the breeder code 12-11-01. 'Fashionably Early Flamingo' has been asexually propagated by stem cuttings in the greenhouses at the same nursery in Zeeland, Mich. The unique characteristics of the new plant have been found to be reproducible and stable in successive generations of asexually propagated and the resultant plants have been found to be identical to the original selection.

No plants of *Phlox* 'Fashionably Early Flamingo' have been sold, in this country or anywhere in the world, prior to the filing of this application, nor has any disclosure of the new plant been made prior to the filing of this application with the exception of that which may have been disclosed within one year of the filing date of this application and was either derived directly or indirectly from the inventor.

BRIEF SUMMARY OF THE PLANT

*Phlox* 'Fashionably Early Flamingo' is unique from its parents and all other tall garden *phlox* or other *Phlox* known to the inventor. The new plant differs from the female parent *Phlox maculata* 'Alpha' by having light lavender-pink flowers fading to pale lavender with age, and broader flower heads on thicker stems, whereas 'Alpha' has lilac-rose colored flowers in a tighter cyme. Compared to the male parent, 'Amethyst Pearl', the new plant is taller, has thicker stems, larger and stiffer foliage flowering, producing larger light lavender-pink flowers with a tiny light purple eye on taller plants with thicker stems. The nearest comparison *phlox* varieties are 'Barsixtytwo' U.S. Plant Pat. No. 22,234 which has shorter broader leaves and flowers of a more red hue for a shorter period, and 'Barsixtyone' U.S. Plant Pat. No. 22,223 which has shorter broader leaves and flowers of a more purple hue for a shorter period. Compared with the sister sibling, 'Fashionably Early Princess' (U.S. Plant Pat. No. 28,680) the new plant is purple-violet and the comparison plant is a lighter hue of violet. 'Fashionably Early Flamingo' differs from all other *phlox* known to the inventor in the following repeatedly observed traits in combination:

1. Plants of compact habit, slowly spreading by short rhizomes, producing clean, glossy, bright-green, lanceolate leaves.
2. Multiple stems produce rounded heads of flowers very early in the season.
3. Sweetly fragrant flowers on strong flexible stems of about 77 to 90 cm tall producing sweetly-fragrant, lavender-pink flower faces.
4. Excellent re-blooming through mid-fall when deadheaded.

BRIEF DESCRIPTION OF THE DRAWINGS

The photographs of the new plant demonstrate the unique traits of 'Fashionably Early Flamingo' and the overall appearance of the plant at two-years old. The colors are as accurate as reasonably possible with color reproductions. Variation in ambient light spectrum, source and direction may cause the appearance of minor variation in color.

DETAILED BOTANICAL DESCRIPTION

Figure 1:
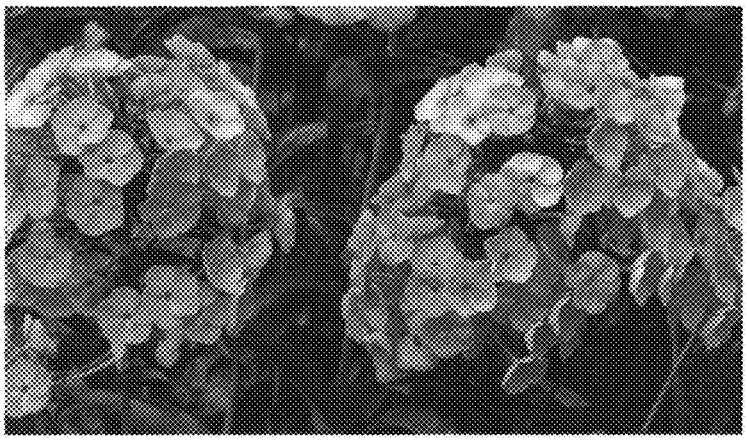
FIG. 1 shows a close-up of the floriferous flower head with flowers and buds.
Figure 2:
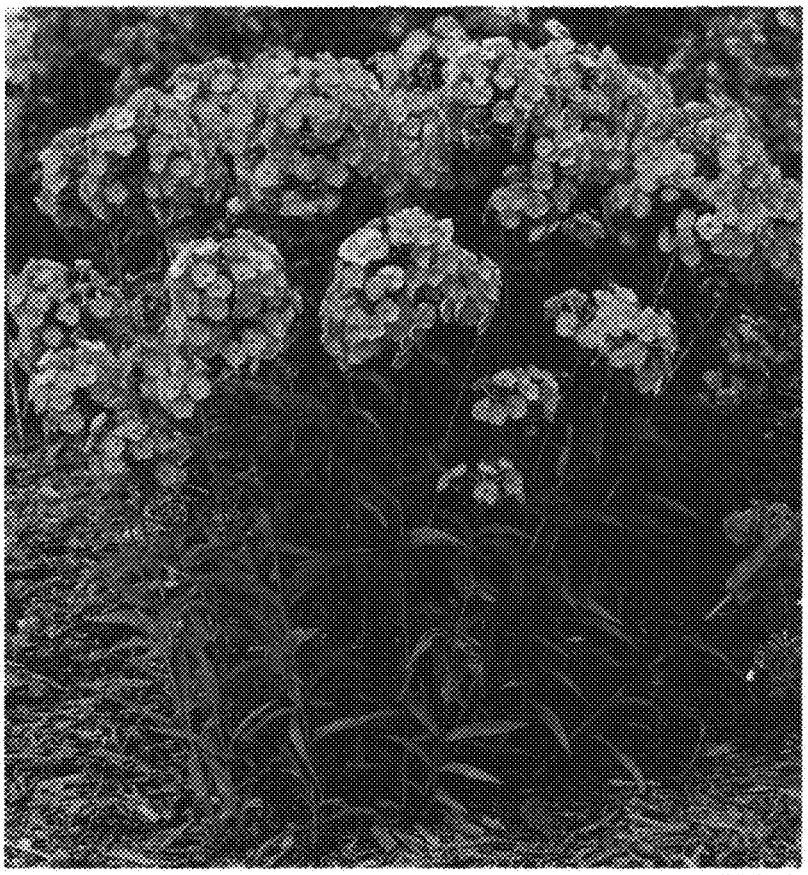
FIG. 2 shows the new plant in flower in the landscape with late spring to early summer foliage.

The following descriptions and color references are based on the 2001 edition of The Royal Horticultural Society Colour Chart except where common dictionary terms are used. *Phlox* 'Fashionably Early Flamingo' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun trial garden of a wholesale perennial nursery in Zeeland, Mich. with supplemental fertilizer and water as needed.

Botanical classification: *Phlox* hybrid;

Parentage: Female or seed parent *Phlox maculata* 'Alpha' (not patented); male or pollen parent *Phlox* 'Amethyst Pearl' U.S. Plant Pat. No. 28,487;

Plant habit: Hardy herbaceous perennial, densely upright, producing about 36 rigid upright stems; about 77.0 to 90.0 cm tall at flowering and about 85.0 cm wide at flowers; flowering begins late spring in Michigan continuing for about 5 weeks and repeating through summer and until heavy frost if deadheaded;

Propagation: Stem cuttings; rooting in about 14 days;

Time to produce finished crop in 3.8 liter pots: About 8 to 10 weeks; moderate rate of growth;

Root: Primary roots to about 1.0 mm thick; secondary fibrous and freely branching; color creamy white to tan depending on soil type;

Leaves: Simple, opposite, lanceolate, entire; glabrous abaxial; puberulent adaxial; lustrous adaxial, matte abaxial; sharply acute apex, rounded base; to about 18.0 cm long by about 3.2 cm wide, average about 14.2 cm long by about 2.5 cm wide;

Leaf color: Young leaf abaxial between RHS 146B and RHS 146C, adaxial nearest RHS 137A; mature leaf abaxial between RHS 146B and RHS 146C, adaxial between RHS 138A and RHS 141A;

Foliage fragrance: None detected;

Veins: Reticulate; glabrous abaxial, puberulent adaxial; midvein about 1.0 mm wide at base, slightly sunken adaxial and costate abaxial;

Vein color: Abaxial midrib nearest RHS 146D, adaxial midrib between RHS N144A and RHS 146D; other adaxial and abaxial veins not noticeable;

Petiole: About 2.0 mm long and 4.0 mm across;

Petiole color: Abaxial nearest RHS 146D, adaxial between RHS N144A and RHS 146D;

Stems: Terete; stiff; strong; upright; sparsely puberulent; average about 72.0 cm long and 3.5 mm diameter at base;

Stem color: Nearest 145A with speckling of nearest RHS 187B in sun exposed distal portion;

Nodes: About 10 per stem below flowers; average internode length about 7.2 cm; shorter proximally and longer distally;

Node color: Nearest RHS 145A;

Flowers: Perfect; salverform, rotate, actinomorphic, typically with five petals; about 3.2 cm long total with tube about 2.8 cm long; face about 2.8 cm across; tube about 2.0 mm diameter at base and 2.8 mm diameter before face; held in a branched compound corymb of about 100 to 150 flowers; attitude upright to outward;

Flower longevity: About 5 days on plant or as cut flower; self-cleaning;

Flower fragrance: Pleasantly sweet;

Buds one to two days prior to opening: Narrowly oblanceolate, to nearly clavate; acute apex with petals twisted about each other; about 2.4 cm long and 2.8 mm diameter in tube and swollen to 4.0 mm diameter toward apex;

Bud color: Tube base nearest 150D, center nearest RHS 145C; swollen apex nearest RHS N82B with petal margins nearest RHS N82D;

Petals: Five, glabrous except pubescent for about 4.0 mm to 6.5 mm from base of inner adaxial tube; margin entire; apex rounded; basal about 2.8 cm fused into tube; rounded limbs to about 1.6 cm across, imbricate petals on either side by about 4.0 mm;

Young petal color: Outer abaxial tube base nearest RHS 150D, outer abaxial tube middle nearest RHS N80B, abaxial face perimeter nearest RHS N80C, surrounding tube nearest RHS 76C; inner adaxial tube base nearest RHS 155D, middle tube between RHS N80B and RHS 78C, throat radiating star lighter than RHS N78B, adaxial face nearest RHS N80B with portion between radiating star and face lighter than RHS N78B;

Mature petal color: Outer abaxial tube base nearest RHS N79D, middle tube between RHS 77B and RHS 77C, abaxial face nearest RHS N80C and lighter than RHS N80D where faded; inner adaxial tube nearest RHS N79D, center eye and portions of covered petal blend between RHS N78B and RHS N78C; petal face nearest RHS 84D; face fading to lighter than RHS N80D;

Androecium:

*Filaments*.—Usually five, fused to inner petals except free in terminal 1.0 mm; varying lengths between 15.0 mm and 20.0 mm above base, less than 0.2 mm in diameter; white, lighter than RHS 155D.

*Anther*.—Five; oblong elliptic; dorsifixed; longitudinal; about 3.0 mm long by 1.0 mm wide; joined at different heights of 2.0, 2.3 and 2.5 mm above base; color nearest RHS 13B.

*Pollen*.—Nearly microscopic, spherical; color nearest RHS 17B.

Gynoecium: One pistil per flower;

*Style*.—Terete; about 2.1 cm long and 0.3 mm diameter when flower is mature; color of base nearest RHS 145C, proximal half nearest RHS N155C.

*Stigma*.—Trifurcate in the distal 2 mm, less than 0.25 mm in diameter; persistent after flower abscission; color nearest RHS 2C.

*Ovary*.—Superior, elliptic, about 2.0 mm long and 0.5 mm diameter; color nearest RHS 6B.

Sepals: Five, glabrous; lanceolate; sharply acute apex, margin entire; individually about 11.0 mm long and 2.0 mm across; fused in basal 6.0 mm forming tube 2.5 mm diameter at base and 5.0 mm diameter at apex;

Sepal color: Abaxial apical 1.5 mm nearest RHS N186A, midsection varying between RHS 138B and RHS N186D with more light exposure, margins about 0.2 mm wide translucent with some pigment nearest RHS N186D; adaxial apex nearest RHS N186A, midsection nearest RHS 138B with slight tinting of nearest RHS 187B and margins about 0.2 mm wide translucent with some blush nearest RHS N78B;

Peduncle: Puberulent, stiff, strong, upright, terete; about 2.5 mm diameter at base of main stem and 1.0 mm diameter of branches; flowering portion about 11.0 cm long with flowers spreading 16.0 cm across the inflorescence;

Peduncle color: Nearest RHS 145A with heavy speckling nearest RHS 187B on exposed portion;

Fruit and seed not observed:

Hardiness and culture: The new plant grows best with plenty of moisture and adequate drainage; hardy to at least from USDA zone 4 through 8.

Disease and pest resistance: *Phlox* 'Fashionably Early Flamingo' demonstrated the excellent powdery mildew resistance under conditions that would normally show symptoms.

I claim:

1. A new and distinct cultivar of hybrid *phlox* plant named *Phlox* 'Fashionably Early Crystal', as herein described and illustrated, especially suitable as a potted plant, for the garden, for attracting hummingbirds and butterflies, and for cut flower arrangements.

* * * * *